United States Patent [19]

Sparks et al.

[11] Patent Number: 5,186,937
[45] Date of Patent: Feb. 16, 1993

[54] COMPOSITION FOR FEEDING RUMINANTS

[75] Inventors: Robert E. Sparks, Kirkwood; Norbert S. Mason, St. Louis, both of Mo.; Pierre Autant; Andre Cartillier, both of Commentry, France; Raymond Pigeon, Francheville, France

[73] Assignee: A.E.C. Societe de Chimie Organique et Biologique, France

[21] Appl. No.: 541,195

[22] Filed: Jun. 22, 1990

Related U.S. Application Data

[63] Continuation of Ser. No. 871,295, Jun. 6, 1986, abandoned.

[30] Foreign Application Priority Data

Jun. 7, 1985 [FR] France .................. 85 08626

[51] Int. Cl.⁵ .............................. A61K 9/14
[52] U.S. Cl. ................... 424/438; 424/475; 424/490; 424/491; 424/493; 424/494; 424/497; 424/498
[58] Field of Search .................. 424/14, 78, 438, 475, 424/490, 491, 493, 494, 497, 498

[56] References Cited

U.S. PATENT DOCUMENTS

| T100,404 | 3/1981 | Wu | 424/78 |
| 4,177,255 | 12/1979 | Donnelly | 424/33 |
| 4,220,153 | 9/1980 | Dresback | 128/260 |

FOREIGN PATENT DOCUMENTS

| 557929 | 10/1982 | Australia |
| 838505 | 5/1976 | Belgium |
| 1289423 | 2/1962 | France |
| 1568930 | 5/1969 | France |
| 2514261 | 4/1983 | France |
| 936386 | 9/1963 | United Kingdom |
| 1217365 | 12/1970 | United Kingdom |

*Primary Examiner*—Thurman K. Page
*Attorney, Agent, or Firm*—Morgan & Finnegan

[57] ABSTRACT

A composition which is stable in a medium in which the pH is greater than or equal to 5.5 and which permits the release of an active substance in a medium in which the pH is less than or equal to 3.5, comprising the active substance, which contains inclusions of, or which is completely or partially covered by, a pH sensitive material whose extent and/or rate of swelling is greater in an acidic medium than in a neutral medium, and a coating of a hydrophobic layer.

6 Claims, No Drawings

COMPOSITION FOR FEEDING RUMINANTS

This application is a continuation of application Ser. No. 871,295, filed Jun. 6, 1986 abandoned.

FIELD OF THE INVENTION

The present invention relates to a new product for feeding to ruminants, which is stable in a medium in which pH is greater than or equal to 5.5 and which permits the release of an active principle in a medium in which the pH is less than or equal to 3.5.

BACKGROUND OF THE INVENTION

In particular, certain biologically active substances, for example drugs or enriched feeds, fed to ruminants can be enzymatically destroyed as they pass through the rumen, the amount of destruction being flavored by the conditions in the rumen, for example residence time (a few hours to several days) and by the pH (from 5 to 6).

It is consequently important to protect these biologically active substances by coatings which are stable at a pH greater than or equal to 5, that is to say which are stable in the rumen of ruminants, which withstand degradation by microorganisms and which permit the release of the biologically active substances in a part of the digestive tract, more especially in the abomasum, in which the pH is less than or equal to 3.5. Whereas the period of protection in the rumen has to be relatively long (several hours to a few days), the release of the active substance in the abomasum must take place within a relatively short time (from a few minutes to 1 or 2 hours).

To obtain such results, it is advantageous to be able to have coatings for the active substances such that they are insoluble in the rumen at a pH of from 5 to 6, but soluble, dispersed or greatly swollen in the abomasum at a pH of less than or equal to 3.5 to release the active substance.

To produce such coatings, it has previously been proposed to use, inter alia, copolymers of maleic anhydride with another monomer, the copolymers being modified by the action of a primary/tertiary diamine on the anhydride groups, thereby forming aminated imide groups which provide the desired solubility, see, for example, French Patent 1,536,774. It has also been proposed to use aminated cellulose derivatives obtained from an unsaturated derivative of cellulose, for example an ether or ester, which is reacted with a nitrogenous compound containing an active hydrogen atom, such as piperidine, morpholine or a secondary amine, see, for example, French Patent 2,081,320.

Furthermore, in British Patent 1,137,214, Australian Patent 45,117, Belgian Patent 885,654, South African Patent Application 70/04,813, French Patent 2,246,572 and U.S. Pat. No. 3,341,505, there are described copolymers of:

a) a neutral ethylenic monomer such as methyl acrylate or methacrylate, styrene, acrylonitrile or vinyl acetate, and b) a diethylenic monomer containing a basic nitrogenous group such as diethylaminoethyl acrylate or methacrylate, morpholinoethyl acrylate or methacrylate or a vinylpyridine.

To coat feeds intended for ruminants, it has also been proposed to use styrene/vinylpyridine copolymers containing hydrophobic substances chosen from fatty acids containing 10 to 32 carbon atoms and polycarboxylic acids comprising 10 to 22 carbon atoms per carboxyl group which improve the protection by reducing the overall sensitivity of the coating film to weakly acidic aqueous media, see, for example, French Patent 2,401,620. In such coating compositions, the hydrophobic substance enables the wettability of the polymer to be decreased but remains devoid of an effect on the release of the active principle in an acidic medium.

In French Patent 2,514,261, a coating is described which consists of a copolymer sensitive to pH variations, chosen from copolymers of styrene with vinylpyridines, and a water-insoluble polymer insensitive to pH variations, chosen from cellulose acetate butyrate, ethylcellulose and cellulose propionate, the latter promoting the release of the active substance at a pH of from 1 to 2.5 and enabling the extractability of the active substance in an aqueous medium to be reduced.

In French Patent 2,401,621, a hydrophobic polymer in which there is dispersed a substance which is soluble in an acidic medium, for example an alkali metal phosphate, dispersed in crosslinked basic polymers, is described.

In U.S. Defensive Publication number T 100,404, a double-layer system is described, in which the active substance is coated with two successive layers consisting of a polymer sensitive to pH variations, such as a styrene/vinylpyridine copolymer, and a hydrophobic substance such as a fatty acid, in different proportions.

The present invention provides a composition which is stable in a medium in which the pH is greater than or equal to 5.5 and which permits the release of an active substance in a medium in which the pH is less or equal to 3.5, comprising the active substance, which contains inclusions of, or which is completely or partially covered by, a pH sensitive material whose extent and/or rate of swelling is greater in an acidic medium than in a neutral medium, and a coating of a hydrophobic layer.

The pH sensitive materials which are especially suitable are basic polymers, salts of natural or synthetic acids or polyacids, proteins, polysaccharides such as polyglucosamines or alginates, or mixtures of any two or more of these. Examples of basic polymers are those containing at least one basic amino group and having a basic nitrogen content of from 2 to 14%, such as aminated derivatives of cellulose, polymers and copolymers of aminated derivatives of acrylic, methacrylic and crotonic acids, and polymers or copolymers of styrene or acrylonitrile with isomers or derivatives of vinylpyridine, such as 2-vinylpyridine, 4-vinylpyridine or 2-methyl-5-vinylpyridine. Examples of salts of natural or synthetic acids or polyacids are calcium carbonate, zinc polymethacrylate or complex polyphosphates of calcium, sodium, aluminium or magnesium. A preferred protein is zein, which can be isolated from maize gluten. Preferred polyglucosamines are chitosan, which can be obtained by deacetylation of chitin which is found in abundance in the shells of crustaceans, and chitosan derivatives.

The most preferred pH sensitive materials are those polymers which contain at least one basic amino group and which have a basic nitrogen content of from 2 to 14%.

These pH sensitive materials can be used alone or mixed, or in combination with adjuvants.

The hydrophobic layer is preferably chosen such that it possesses a texture which permits the diffusion or penetration of the external liquid medium. In addition to a low permeability to water, the hydrophobic layer must have suitable physical properties, such as high tensile strength and yield strength, and good film-forming qualities.

Examples of hydrophobic substances which make up the hydrophobic layer are fats, paraffin waxes, natural waxes (carnauba wax, beeswax), synthetic waxes (polyethylene wax), polymers such as polyethylene, polypropylene, polybutenes, polyisobutenes, polypentenes, polystyrene, polyvinyl chloride or fluoride, polyvinylidene chloride or fluoride, polyphenylenes, polyphenylene oxides, polybutadiene, polyisoprene or polychloroprene, polyvinyl acetate, water-insoluble cellulose derivatives and latexes; the hydrophobic substances can be used alone or in a mixture, so as to obtain an external layer having the desired mechanical properties.

To obtain a thin coating, the hydrophobic substances should have a suitable viscosity in the molten state or in solution. It is especially advantageous that the viscosity in the molten state is from 20 to 100 poises (2 to 10 Pas). When the viscosity is too low, coating is unsatisfactory. When the viscosity is too high, the coating layer is too thick and agglomeration phenomena arise.

In order to lower the viscosity, it is possible to mix substances which are liquid at room temperature with solid substances. The liquid substances should be compatible with the polymer.

Preferred hydrophobic substances are the readily melted mixtures of polyethylene wax, paraffin and hydrocarbon resins.

In the compositions according to the invention the pH sensitive material preferably represents from 0.5 to 30% of the weight of the active substance and any adjuvants which may be present in association with the active substance. The external coating layer, the average thickness of which is preferably from 5 to 200 micrometers, depending on the size of the granule to be coated, preferably represents from 1 to 50% of the total weight of the composition.

The compositions of the present invention can contain adjuvants to facilitate the preparation of the compositions or to improve their physicochemical characteristics. It may be advantageous to add plasticizers (triacetin, propylene glycol), lubricants (magnesium stearate), binding agents (polyvinylpyrrolidone, polyvinyl alcohol, gelatin), antistatic agents (triglycerides having polyoxyethylenated chains), anti-caking agents (silica, calcium carbonate), fungicides, emulsifiers (oxyethylenated sorbitan esters, sugar glycerides), compatibility agents (natural or semi-natural gums such as alginates, gum tragacanth, pectins, carragheenates, xanthan gum), cellulose ethers (carboxymethyl-, methyl- or hydroxypropylcellulose), inorganic fillers (inorganic salts), sugars, starches or proteins. These adjuvant derivatives generally represent only a few percent by weight of the total weight of the coating.

The active substances can be therapeutic or nutrient substances such as drugs, vitamins (vitamin A, vitamin E) or amino acids, preferably essential amino acids (lysine, methionine) intended for oral administration to ruminants. The therapeutic or nutrient substances are generally in solid form; when the therapeutic or nutrient substances are in liquid form, they may be adsorbed on an inert carrier such as silica, a silicate, an alumina, an aluminate, a silicoaluminate or starch.

The compositions according to the present invention are preferably granules, which are generally spherical or cylindrical, their average diameter being from 0.05 to 5 mm. They can be prepared by application of the known techniques of granulation and coating.

In general, it is necessary to mix the active substance with, or to completely or partially pre-coat it by, the pH sensitive material and then to coat the product thereby obtained, generally in the form of granules, with the hydrophobic layer.

The mixture of the active substance with the pH sensitive material can be made by mixing the finely divided substance and material and then granulating the product obtained.

The partial or complete pre-coating can be performed by the customary coating techniques, such as encapsulation in a fluidized bed, immersion or coacervation.

To perform the coating with the hydrophobic layer various techniques can be used. It is possible to perform the coating, for example, in a fluidized bed, by immersion, by adsorption in a liquid medium or by coacervation. It is also possible to perform the coating with the molten or dissolved hydrophobic substance by projecting a suspension of the pretreated active substance in the molten substance, or the substance dissolved in a suitable organic solvent in which the pretreated active substance is insoluble, onto a flat or concave disc, optionally grooved, rotating at a specified speed and heated by means of hot air, in general to a temperature 20° above the solidification temperature of the hydrophobic composition. In general, the pretreated composition containing the active substance is dispersed in twice its weight of hydrophobic composition. The excess hydrophobic substance forms small particles which remain in the vicinity of the disc, whereas the required coated particles are ejected further away. This results in systematic separation of the required coated particles and the particles of hydrophobic substance in the course of carrying out the process. The excess hydrophobic substance can be recycled.

EXAMPLES

The examples which follow illustrate how the invention may be put into practice.

COMPARATIVE EXAMPLE 1

Methionine in the form of spherical cores containing 98% of methionine and having a diameter of from 0.5 to 0.63 mm are pre-coated with a 2-vinylpyridine/styrene (70:30) copolymer using a fluidized bed technique to obtain pre-coated granules for which the pre-coating ratio (weight of coating/weight of core×100) is 4.25% and the thickness of the pre-coating layer is in the region of 5 micrometers.

COMPARATIVE EXAMPLE 2

The procedure at Example 1 is carried out to obtain pre-coated methionine granules for which the pre-coating ratio is 7% and the thickness of the pre-coating layer is in the region of 8 micrometers.

COMPARATIVE EXAMPLE 3

The procedure of Example 1 is carried out to obtain pre-coated methionine granules for which the pre-coating ratio is 13.5% and the thickness of the pre-coating layer is in the region of 15 micrometers.

EXAMPLE 4

52 g of the pre-coated granules obtained in Example 1 are coated by projecting a suspension of the granules in 60 g of a hydrophobic composition consisting of bareco C 1035 wax (30 g), paraffin wax having a melting point of from 58° to 63° C. (10 g), USI NA 601 polyethylene (20 g) and 25 cm³ of an octane/heptane (1:1 by volume) mixture, at a temperature of 90° C., onto a disc rotating at 2150 rpm.

12.6 g of coated methionine granules containing 64.7% of methionine and having a diameter of from 0.5 to 1 mm are thereby obtained. 83% of the granules obtained have a diameter of from 0.59 to 0.86 mm.

EXAMPLE 5

The procedure of Example 4 is carried out but starting with 52 g of the pre-coated methionine granules obtained in Example 2, working at a temperature of 96° C. and a speed of rotation of the disc of 2160 rpm. 15.9 g of coated methionine granules containing 61.6% of methionine and having a diameter of from 0.5 to 1 mm are obtained.

EXAMPLE 6

The procedure of Example 4 is carried out but starting with 52 g of the pre-coated methionine granules obtained in Example 3, working at a temperature of 98° C. and a speed of rotation of the disc of 2160 rpm.

12.1 g of coated methionine granules containing 60.1% of methionine and having a diameter of from 0.5 to 1 mm are obtained.

EXAMPLE 7

52 g of pre-coated methionine granules obtained in Example 1 are coated with 100 g of a hydrophobic composition consisting of polywax 500 (50 g), paraffin wax (30 g) and USI NA 597 polyethylene (20 g), working at a temperature of 124° C. and a speed of rotation of the disc of 2160 rpm.

17.6 g of coated methionine granules containing 65.5% of methionine and having a diameter of from 0.5 to 1 mm are thereby obtained.

EXAMPLE 8

The procedure of Example 7 is carried out but starting with 52 g of pre-coated methionine granules obtained in Example 2 and 100 g of hydrophobic composition, working at 132° C. and a speed of rotation of the disc of 2160 rpm.

17.7 g of coated methionine granules containing 61.6% of methionine and having a diameter of from 0.5 to 1 mm are obtained.

EXAMPLE 9

The procedure of Example 7 is carried out but starting with 52 g of pre-coated methionine granules obtained in Example 3 and 100 g of hydrophobic composition, working at a temperature of 121° C. and a speed of rotation of the disc of 2160 rpm.

17 g of coated methionine granules containing 59.3% of methionine and having a diameter of from 0.5 to 1 mm are obtained.

EXAMPLE 10

150 g of pre-coated methionine granules obtained in Example 1 are coated with 300 g of a composition consisting of polywax 500 (150 g), paraffin wax (90 g) and USI NA 597 polyethylene (60 g), working at a temperature of 124° C. and a speed of rotation of the disc of 2160 rpm.

82.6 g of coated methionine granules containing 63% of methionine and having a diameter of from 0.5 to 1 mm are thereby obtained.

EXAMPLE 11

The procedure of Example 10 is carried out but starting with 155 g of pre-coated methionine granules obtained in Example 2 and 300 g of hydrophobic composition, working at a temperature of 118° C. and a speed of rotation of the disc of 2160 rpm.

85 g of coated methionine granules containing 64.8% of methionine and having a diameter of from 0.5 to 1 mm are thereby obtained.

EXAMPLE 12

The procedure of Example 10 is carried out but starting with 165 g of pre-coated methionine granules obtained in Example 3 and 300 g of hydrophobic composition, working at a temperature of 102° C. and a speed of rotation of the disc of 2160 rpm.

51.2 g of coated methionine granules containing 55.3% of methionine and having a diameter of from 0.5 to 1 mm are obtained.

EXAMPLE 13

Spherical methionine granules having a diameter of between 0.5 and 0.63 mm are pre-coated, using the fluidized bed technique, with 7% of methacrylate/-dimethylaminoacetate copolymer (Eudragit E, N. D. ROHM PHARMA), in such a way that the pre-coated layer has a thickness in the region of 8 micrometers.

The granules thereby obtained are coated with a molten mixture of polywax 500 (50), paraffin wax (30) and USI NA 597 polyethylene (20). Coated granules containing 56% of methionine and having a diameter of from 0.5 to 1 mm are thereby obtained.

To demonstrate the sensitivity of the compositions according to the invention to pH variations, tests are carried out which enable the release of the active substance to be measured at different pH values as a function of time.

More especially, the release of the active substance is examined by stirring, under specified conditions, a known amount of granules in a buffered medium maintained at constant pH at a temperature of 40° C. The amounts of active substance released at different pH values, in particular at pH 6 and at pH 2, are compared as a function of time.

The results obtained for the compositions prepared in the Examples are collated in percentages in Table 1.

TABLE 1

| EXAMPLE | RELEASE AFTER ½ H. at | | RELEASE AFTER 2 H. at | | RELEASE AFTER 3 H. at | | RELEASE AFTER 24 H. at | |
|---|---|---|---|---|---|---|---|---|
| | pH 6 | pH 2 | pH 6 | pH 2 | pH 6 | pH 2 | pH 6 | pH 2 |
| 1 | 92.7 | 100 | 100 | 100 | 100 | 100 | 100 | 100 |
| 2 | 48.9 | 100 | 98.8 | 100 | 100 | 100 | 100 | 100 |
| 3 | 11.3 | 98.1 | 55.4 | 100 | 68.8 | 100 | 96.5 | 100 |
| 4 | 1.3 | 42.5 | 8.4 | 91.5 | 15.2 | 94.9 | | |
| 5 | 1.3 | 95.0 | 4.6 | 100 | 5.6 | 100 | | |
| 6 | 1.3 | 89.9 | 2.5 | 100 | 3.6 | 100 | 18.1 | 100 |
| 7 | 1.3 | 48.8 | 2.5 | 91.6 | 3.6 | 93.9 | 61.0 | 99.0 |
| 8 | 0.6 | 41.2 | 2.5 | 87.8 | 2.5 | 91.3 | 40.4 | 98.4 |
| 9 | 1.3 | 47.8 | 1.9 | 77.2 | 2.5 | 79.5 | 20.1 | 93.3 |
| 10 | 1.9 | 4.5 | 1.3 | 18.4 | 2.4 | 23.0 | 49.3 | 74.0 |
| 11 | 2.5 | 15.3 | 2.5 | 55.3 | 2.5 | 62.2 | 40.7 | 83.7 |
| 12 | 1.2 | 51.9 | 1.9 | 91.8 | 2.9 | 96.3 | 21.9 | 100 |
| 13 | 2 | 30 | 5 | 55 | 10 | 62 | | |

The efficacy in vivo of the compositions according to the present invention is demonstrated in the following tests:

1) Test of blood methionine level

A regular dose of methionine, referred to the metabolic weight of the animal, is administered for ingestion daily for 7 days to a ewe. Blood samples are drawn on days 6 and 7, and the blood methionine is determined by the method of Stein and Moore, J. BIOL. CHEM., 192, P. 663 (1951). The blood methionine levels produced by protected or unprotected methionine are compared under identica supplementation conditions.

The results are collated in Table II.

TABLE II

| COMPOSITION | SUPPLEMENTATION (METHIONINE EQUIVALENT in g/kg of METABOLIC WEIGHT per DAY) | BLOOD METHIONINE LEVEL (mg of METHIONINE PER g of BLOOD) |
| --- | --- | --- |
| Unprotected methionine | 0.38 | 0.36 |
| Example 7 | 0.38 | 2.0 |
| Example 8 | 0.38 | 1.50 |
| Example 9 | 0.30 | 1.50 |

2) Test of the concentration of free methionine in the duodenal juice.

Methionine is administered for ingestion in regular doses, under standard conditions, to ewes with a artificial duodenal fistula. On days 4 and 5 of the supplementation, samples of the duodenal juice are taken and the free methionine therein is determined.

The results are collated in Table III.

TABLE III

| COMPOSITION | SUPPLEMENTATION g of METHIONINE/DAY | FREE METHIONINE (mg per kg of DUODENAL JUICE) |
| --- | --- | --- |
| Unprotected methionine | 10 | 51 |
| Example 7 | 10 | 228 |
| Example 8 | 10 | 362 |
| Example 9 | 10 | 241 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. An at least partly coated composition having improved release characteristics at pH of less than or equal to 3.5 which is suitable for use in feeding ruminants and which is stable in a medium in which the pH is greater than or equal to 5.5 and which permits the release of an active substance in a medium in which the pH is less than or equal to 3.5, comprising the active substance, which contains inclusions of, or which is completely or partially covered by a pH sensitive material which is a polymer containing at least one basic amino group and which has a nitrogen content of from 2 to 14%, and an outer coating consisting of a hydrophobic material which is non-sensitive to pH.

2. A method of treatment of a ruminant comprising administering to the ruminant a composition as defined in claim 1.

3. A composition according to claim 1, wherein the pH sensitive material is a copolymer of styrene with an isomer or derivative of vinylpyridine.

4. A composition according to claim 1, wherein the hydrophobic layer comprises a fat, a paraffin wax, a natural wax, a synthetic wax, a polymer derived from ethylene, isobutylene or vinyl acetate, a water-insoluble cellulose derivative or a mixture of at least two of these.

5. A composition according to claim 1 wherein the active substance is a drug, a vitamin or an essential amino acid.

6. A composition according to claim 5, wherein the active substance is lysine or methionine.

* * * * *